US010809275B2

(12) United States Patent
Hurwitz et al.

(10) Patent No.: US 10,809,275 B2
(45) Date of Patent: Oct. 20, 2020

(54) VERIFICATION PIPETTE AND VISION APPARATUS

(71) Applicant: Kobra BioSolutions, LLC, Reno, NV (US)

(72) Inventors: Jeffrey P. Hurwitz, Reno, NV (US); Lloyd Andrew Corkan, Louisville, CO (US)

(73) Assignee: Kobra Biosolutions, LLC, Reno, NV (US)

( * ) Notice: Subject to any disclaimer, the term of this patent is extended or adjusted under 35 U.S.C. 154(b) by 424 days.

(21) Appl. No.: 15/631,168

(22) Filed: Jun. 23, 2017

(65) Prior Publication Data
US 2017/0370956 A1    Dec. 28, 2017

Related U.S. Application Data

(60) Provisional application No. 62/354,327, filed on Jun. 24, 2016.

(51) Int. Cl.
*G01N 35/10*    (2006.01)
*G01N 1/10*    (2006.01)
(Continued)

(52) U.S. Cl.
CPC .......... *G01N 35/1016* (2013.01); *B01L 3/021* (2013.01); *B01L 9/56* (2019.08); *C12M 1/34* (2013.01); *C12Q 1/6806* (2013.01); *G01N 1/10* (2013.01); *G01N 35/1011* (2013.01); *G06K 9/00771* (2013.01); *G06K 9/36* (2013.01); *G06T 7/0012* (2013.01); *B01L 2200/143* (2013.01); *G01N 1/00* (2013.01); *G01N 35/00* (2013.01);
(Continued)

(58) Field of Classification Search
None
See application file for complete search history.

(56) References Cited

U.S. PATENT DOCUMENTS 3,719,087 A    3/1973  Thiers
3,834,240 A    9/1974  Kenney
(Continued)

FOREIGN PATENT DOCUMENTS

EP          3222354       9/2017
WO    WO 2015/172971    11/2015
WO    WO 2016/035180     3/2016

*Primary Examiner* — Jill A Warden
*Assistant Examiner* — Brittany I Fisher
(74) *Attorney, Agent, or Firm* — Heisler & Associates (57) ABSTRACT

Manually operated pipettors, widely used in clinical, forensics, pharmaceutical research, hospital and biotech laboratories to transfer small volumes of liquid, may be subject to positional errors, operator use errors and hidden performance degradation. Manual pipette performance cannot be accepted without monitoring and reporting. This invention concerns a computer controlled vision tracking and lighting system working in conjunction with a sensor controlled fluid dispensing device and controller to confirm pipette tip positional locations during aspiration and dispensing operations with automatic monitoring of liquids entering and leaving a pipette apparatus to digitally track a manual pipetting operation with a digital output file of validated liquid transfer results. The invention may also monitor possible error conditions and prevent improper liquid transfers during the manual process.

16 Claims, 6 Drawing Sheets

(51) Int. Cl.
  *B01L 3/02* (2006.01)
  *G06K 9/36* (2006.01)
  *G06T 7/00* (2017.01)
  *B01L 9/00* (2006.01)
  *G06K 9/00* (2006.01)
  *C12M 1/34* (2006.01)
  *C12Q 1/6806* (2018.01)
  *G01N 1/00* (2006.01)
  *G01N 35/04* (2006.01)
  *G01N 35/00* (2006.01)

(52) U.S. Cl.
  CPC . *G01N 35/1065* (2013.01); *G01N 2035/0494* (2013.01); *G06K 9/00* (2013.01); *G06T 2207/30004* (2013.01)

(56) References Cited

U.S. PATENT DOCUMENTS

| | | | |
|---|---|---|---|
| 3,853,012 A | 12/1974 | Scordato | |
| 3,963,061 A | 6/1976 | Kenney | |
| 4,369,665 A | 1/1983 | Citrin | |
| 4,780,833 A | 10/1988 | Atake | |
| 4,821,586 A | 4/1989 | Scordato | |
| 4,896,270 A | 1/1990 | Kalmakis | |
| 7,640,787 B2 | 1/2010 | Curtis | |
| 7,870,797 B2 | 1/2011 | Curtis | |
| 8,030,080 B2* | 10/2011 | Spence | B01L 3/0293 436/43 |
| 8,096,197 B2 | 1/2012 | Curtis | |
| 8,486,714 B2* | 7/2013 | Favuzzi | G01N 1/30 422/50 |
| 8,850,903 B2 | 10/2014 | Curtis | |
| 2005/0084423 A1* | 4/2005 | Zarowitz | B01L 3/021 422/504 |
| 2006/0105359 A1 | 5/2006 | Favuzzi | |
| 2007/0177778 A1* | 8/2007 | Massaro | G01N 35/1016 382/128 |
| 2008/0227663 A1* | 9/2008 | Tisone | B01J 19/0046 506/39 |
| 2009/0049933 A1 | 2/2009 | Decaux | |
| 2009/0055131 A1* | 2/2009 | Bukshpan | B01L 3/02 702/187 |
| 2010/0226825 A1 | 9/2010 | Beckey | |
| 2012/0291567 A1* | 11/2012 | Homberg | B01L 3/0237 73/864.13 |
| 2012/0309636 A1* | 12/2012 | Gibbons | B01L 3/0275 506/9 |
| 2013/0150266 A1* | 6/2013 | Tisone | B01J 19/0046 506/37 |
| 2013/0280143 A1* | 10/2013 | Zucchelli | B25J 9/1697 422/501 |
| 2014/0079871 A1* | 3/2014 | Lu | H05K 3/3484 427/8 |
| 2014/0260696 A1* | 9/2014 | Criswell | B01L 3/021 73/864.01 |
| 2015/0060700 A1* | 3/2015 | Bjornson | B01L 3/0241 250/461.1 |
| 2015/0127157 A1* | 5/2015 | Matsukuma | B25J 9/1682 700/258 |
| 2016/0279630 A1* | 9/2016 | Fracchia | B01L 3/0217 |

* cited by examiner

VERIFICATION PIPETTE AND VISION APPARATUS

CROSS-REFERENCE TO RELATED APPLICATIONS

This application claims benefit under Title 35, United States Code § 119(e) of U.S. Provisional Application No. 62/354,327 filed on Jun. 24, 2016.

FIELD OF THE INVENTION

The present invention generally relates to handheld devices for transferring and measuring liquids. More specifically, the present disclosure is directed to a handheld pipette apparatus and vision system for accurately drawing measured amounts of liquid from and accurately dispensing liquid into a microplate, well, tray or test tube as well as tracking and reporting positional location of the handheld pipette apparatus, such as for verification and control purposes.

BACKGROUND OF THE INVENTION

Current handheld electronic pipettes are manually operated and do not track or otherwise output information regarding where liquid was removed from (aspirated) or, where the liquid was dispensed.

For instance, in typical manual handheld pipette devices, an operator manually fills the pipette tip by pressing a valve button on the pipette device to create a suction in order to draw (aspirate) the liquid into the pipette tip. An operator typically precedes aspiration by manually adjusting a rotary mechanism on the pipette device that represents a volume target set by the rotary mechanism. The operator is then required to position the filled pipette tip over a particular location on a microplate or at a particular test tube. Once the device is in position, the operator manually depresses another valve button to dispense the previously drawn aliquot of liquid into the well. The operator may also be required to manually input that the task was completed into a database of some sort (computer based, paper based, etc.). However, there is no way to validate whether the correct liquid, in the correct locations (and amounts) were present when liquid, was aspirated from one source and when the liquid was dispensed at a destination.

Manual electronic handheld pipette devices do not fare much better. Typically, electronic handheld pipette devices include an electrical control unit mounted to the handheld pipette device. These devices typically also include an electronic keypad and a screen for selecting a pipette operating mode and for entering certain information regarding the operation of the device.

However, like the manual non-electric handheld pipette described above, electronic handheld pipette devices use the same basic principal to aspirate and dispense liquids. For example, a motor driving a syringe of the pipette device is calibrated to draw a particular amount of liquid from a source based on movement of the motor. Once drawn, the liquid may be placed in another location. However, nothing tracks the location of the pipette when aspirating and/or dispensing liquid. Also, the parameters that equate the movement of the motor to the volume of the liquid drawn fall out of calibration and can become inaccurate due to the wearing of internal seals, so that volume information loses reliability.

A need thus exists for a system which tracks position of a pipette, especially during the liquid transfer steps of aspiration and dispensing, such that location accuracy can be verified. One problem such a system would address is the problem of verifying that correct samples were correctly processed by laboratory technicians, so that lab results can be more reliably certified, such labs could be crime investigation labs, medical testing labs, research labs, etc. all of which would benefit from a more highly and reliably certified lab results product. Errors due to negligence, overwork, insufficient training, intentional malfeasance, improper calibration, equipment failure, and other causes can all potentially be addressed by such a system.

SUMMARY OF THE INVENTION

Disclosed herein is a system for automatically recognizing and determining whether liquid aspiration and dispensing operations of a handheld pipette apparatus conform to proper procedures, especially as to pipette tip location, and also potentially as to volume transferred. The system may be configured with either or both a single channel handheld pipette apparatus and or a multi-channel high speed pipette apparatus, for example, an eight channel handheld with 8 mm spacing to access ninety-six well microplate labware could be provided, in one embodiment, or a two-dimensional mega channel pipette apparatus with an even larger number of tips could be provided, generally matching the two-dimensional spacing of wells on a microplate or an array of test tubes.

The system described herein includes a vision system that automatically tracks and determines whether the handheld pipette apparatus is in a correct location prior to aspiration and dispensing of liquid. The vision system and/or the handheld pipette apparatus may also be configured to automatically determine whether the amount of liquid aspirated or dispensed by the handheld pipette apparatus is correct. If there is an error, software associated with the system may automatically notify the operator of the error or otherwise track and/or document the error.

The system will document and report one or more aspiration and dispense steps (location and/or volume), and can also report on a mix step, tip attachment/ejection, and optionally storing a picture (or video) of each of the steps in an assay, recipe or other multi-step protocol.

More specifically the single and or multi-channel handheld pipette apparatus described herein includes a real-time, closed loop monitoring system that ensures that the pipette tip of the handheld pipette apparatus is automatically filled at a desired location and preferably also to a desired fill volume. Once filled, the operator moves the handheld pipette apparatus over the destination well or tube as required by the protocol or method to dispense the desired uniform aliquots of liquid from the tip with monitoring of the dispense location. The handheld pipette apparatus itself, preferably monitors the flow rate of the liquid. As such, the amount of liquid that is received into the pipette tip and that flows out of the pipette tip may be tracked and validated electronically as part of the validation process, along with pipette tip position.

In some implementations, the vision system associated with the single and or multi-channel handheld pipette apparatus includes a lighting system and associated logic that helps the vision system recognize and determine when the handheld pipette apparatus, or the pipette tip of the handheld pipette apparatus, is in a proper source container or other proper target location and whether the container is the correct container. The vision system also validates the actual position of the handheld pipette apparatus when liquid is aspirated and dispensed. The system may also be configured to digitally output an image (or series of images or video file(s)), or other associated data, of the pipette tip when it is in the liquid transfer position. The system is also configured to recognize or otherwise determine which container (e.g., which well, test tube etc.) the liquid was transferred from/to.

More specifically, the handheld pipette apparatus of the present disclosure includes a programming controller apparatus that monitors the filling and dispensing of the liquid from the pipette tip. In some embodiments, the handheld pipette apparatus is connected to a programming controller apparatus by a flexible cord that includes, among other features, two or more flexible air hoses. At least one of the air hoses is a vacuum tube that assists with aspiration while the other air hose assists exerts pressure for dispensing. The pipetting controller is typically communicatively coupled to a computer system for programming and monitoring.

The handheld pipette apparatus also includes various buttons that control various operations associated with the handheld pipette apparatus. For example, the buttons may control aspirating and dispensing the liquid, mixing and tip attachment or ejection. The handheld pipette apparatus may also include a visualization screen that notifies the operator of run parameters, errors and actual volumes collected and/or dispensed.

The handheld pipette apparatus may also include various rings (e.g., UV rings or various other color differential rings) that may be used in conjunction with the vision system. For example, the rings may be used to differentiate the handheld pipette apparatus from a background of a laboratory or other facility in which the handheld pipette apparatus is being used. The various rings act to increase the accuracy of the readings of the vision system.

The rings may also be used to generate or otherwise determine a three-dimensional position of the handheld pipette apparatus with respect to a staging area of the system. This positional information is processed in real time and may generate a three-dimensional graphic for the operator to visualize on the computer monitor during system operation. The handheld pipette apparatus may also include a sensor that detects whether the handheld device is in use.

The handheld pipette apparatus preferably includes movement sensors that can detect functional information, such as one or more of whether the handheld is in operation, detect operational errors in the handheld apparatus such as; apparatus is dropped, apparatus is tilted with liquid beyond a software safety limit parameter, apparatus is shaken beyond a software safety limit parameter or apparatus is mishandled according to software safety limit parameters. The software safety limit parameters are preferably preset and programmable.

As briefly discussed above, the handheld pipette apparatus may be integrated or otherwise associated with a vision and lighting system. The vision and lighting system may be also be integrated or otherwise associated with a lab bench workspace or staging area that enables an operator to load pipette tips and/or liquid samples in determined positions in order to process them under a target area of the vision and lighting system.

In some embodiments, the workspace includes any number of programmable locations that may include replacement and specialty pipette tips, liquid containers, test tube racks, microtube racks, microplates and other labware. The workspace may also include a single or multiple camera vision system, and a single or multiple source lighting system attached to or otherwise associated with the workspace. In some embodiments, the handheld pipette apparatus controls the activation and deactivation of the lighting system and/or the vision system. The handheld pipette apparatus may also include an integrated light and/or vision system.

In some embodiments, the system and the associated handheld pipette apparatus may be used in multiple modes. For example, the system may include a live mode and a recipe mode among others.

When a user is starting the system, the operator is preferably required to log into the system. The system may use the vision system and/or the built-in camera on the monitor computer system to take and store a picture of the user and the system for further validation reporting. This login also sets a level of user (e.g. "manager," "administrator") as to what access that operator has in the system.

In a "live mode," there are no pre-set or validated methods to load into the system. Live mode is meant for the user to be able to process samples at will and have the system just follow the operator and document what the operator processes and where. An operator of the system may manually enter the type of labware that is currently being used. The operator may then position or otherwise place the labware on the staging area. A camera or other component of the vision system may scan for a deck layout and any and all bar codes on the labware. The operator may input the desired aspiration and dispensing volumes in the computer via keyboard, a graphical user interface, or on the handheld pipette apparatus. Once the values have been entered, the transfer of liquids may commence.

More specifically, once the data is provided, the system automatically generates validation results of liquid obtained from the source labware and/or the destination labware. More specifically, the system may determine which source wells/tubes liquid was drawn from (using for example, bar codes on the labware with pictures of the deck with the disposable tip in the labware), the aspiration volumes, destination labware into which the liquid was placed or mixed (using for example, bar codes on the labware with pictures of the deck with the disposable tip in the labware) as well as dispensing volumes. This collected information may then be stored locally, remotely, on a network drive, and so on.

The operator may also operate the system in a "recipe" mode. In the recipe mode, the operator may be required to log into the system (or a remote database of system support information, such as recipes to be followed by an organization in a standardized manner). The system may store saved recipes (also called "assays" or "protocols") or methods for drawing and dispensing liquid. In some embodiments, the recipes use a predetermined and/or validated set of transfer volumes along with a specific deck configuration for location of test tubes and wells. This configuration may include what tips, plate trays, liquid containers or test tubes will be loaded into a staging area, so it can be viewed and validated by the vision system.

The operator may then move the handheld pipette apparatus from its holder. Removal of the handheld pipette apparatus typically activates the vision system. The vision system may visually verify or confirm that the deck layout matches the selected recipe/method. That is, the vision system determines whether the various labware required by the recipe is being used and is in the proper position. This may be done by scanning or otherwise determining/detecting visual identifiers (e.g., bar codes) on the labware and comparing the current configuration to the expected configuration (e.g., the configuration of labware required by the recipe). The operator may then start to transfer the liquids as required. The pipette itself can initially be used as a "probe" to verify and calibrate the position of the pipette relative to the microplates, test tubes, and other locations.

As with the live mode described above, the system may automatically generate validation results of source container, source wells/tubes, aspiration volumes, destination containers, destination wells/tubes and dispensing volumes along with pictures during each operation. The information collected during the recipe mode may then be stored locally or on a networked drive or uploaded to a server or to a remote server or other database for archiving.

In some embodiments, the system supports dual positional recognition validation. For example, the handheld pipette apparatus may include various buttons that when pressed or otherwise actuated, causes the vision and lighting system to activate. Activation of the vision system and lighting system acts to validate and/or record the well/tube location in the staging area.

In some embodiments, the vision system uses a two stage validation process. In the first stage, the vision system uses two or more cameras (in some instances, the cameras are located at 90° positions with respect to the staging area or at an angle needed to triangulate handheld positional locations) to capture pipette tip location within the systems deck. For example, the cameras may use UV rings or differential color rings to determine best where the tip of the pipette is.

A recognition software and computer program uses the captured images from the cameras to extrapolate a three-dimensional position of the handheld pipette apparatus over the staging area to calculate the position of the handheld pipette apparatus with respect to the labware on the staging area.

Optionally but preferably, a second stage includes calculating the position of the tip in a particular well through the camera vision system. In some embodiments, the vision system determines the position of the pipette tip of the handheld pipette apparatus by determining or otherwise recognizing the corners of the staging area and/or using a pre-saved plate map. The actual image of the pipette tip in the well is used to calculate the well or tube position relative to the labware being accessed. This can them be compared to the desired location. Once this comparison is complete, a computing device or the handheld pipette apparatus may notify the operator that the handheld pipette apparatus is in the correct location.

The system described herein also includes or otherwise provides error prevention software. This software monitors the various recipes and the processes of the operator to ensure that errors are not committed. For example and as discussed above, in the recipe mode, a specific set of liquid transfers may need to be completed. As such, the system will monitor the various locations of the handheld pipette apparatus during the transfer operations and notify the operator when a liquid handing task is preformed correctly and/or incorrectly. When the operator is notified of an incorrect position of the handheld pipette apparatus, the system may require the operator to correct the position of the handheld pipette apparatus (e.g. using the vision system) before liquid enters or leaves the tip of the handheld pipette apparatus. Such a system can be used in "dry runs" as a training tool and to keep track of user proficiency.

In some embodiments, the vision system and/or the positional recognition software may be activated by the handheld pipette apparatus when a button is actuated in order to dispense, aspirate, and/or mix liquids in the pipette tip. In some embodiments, actuation of the button on the handheld pipette apparatus may cause the vision system to capture an image of the pipette tip to ensure the pipette tip is contained within the proper well or tube. Once the image is captured, the system may analyze the image using the recognition tools described above to determine whether the operator is correctly following the recipe. If the operator is incorrectly performing the recipe (e.g., the handheld device is in the wrong position, in the wrong well etc.) the system notifies the operator and liquid will not be moved into or out of the pipette tip until the operator takes corrective action. The operator notification may be in multimode where the button on the handheld is red for disabled or green for abled while the system computer monitor mirrors this same condition.

In some embodiments, the handheld pipette apparatus of the present disclosure may be configured to monitor itself and diagnose whether a liquid handling task is being correctly performed, whether there is enough liquid in a tip of the handheld pipette device, whether there is air in the sample and/or whether air is present in the sample, whether the well or test tube is empty and so on. The handheld pipette apparatus and/or the vision system may also determine whether a clot or clog is present in the tip of the handheld pipette apparatus such that improper liquid handling is prevented. This may be accomplished by taking an image of the tip and determining whether a blockage exists, by measuring actual flow rate versus expected flow rate of liquid to and from the pipette tip and so on. The handheld pipette apparatus may also monitor itself and recognize and/or diagnose a malfunction and create an error condition during a liquid handling event to prevent further use until the malfunction is fixed or required service is performed on the equipment.

Since the handheld pipette apparatus monitors itself, it may perform various calibrations in real time during every liquid handling phase or process. In some embodiments, the handheld pipette apparatus includes sensors that monitor the flow rate of liquid into and out of the pipette tip. The sensor may also measure the temperature of the liquid which may affect the flow rate. In some embodiments, the handheld pipette apparatus includes a valve that controls the flow of the liquid. The valve remains open until the liquid has flowed into the tip under the physical properties of the liquid. The valve may be configured to automatically close once the target volume has been aspirated or dispensed.

The system monitors and reports that a new or clean tip is attached each time a new liquid is accessed. The handheld pipette apparatus has a sensor that detects tip attachment and tip ejection and will activate the system vision system. The vision system can validate any bar code on the tip box and record the tip type and size of the tip attached, as well as tip manufacture and lot number. Such information can assist in the case of a tip "recall" or other manufacturing issue. The system will also record the tip ejection and the position the tip was ejected into, for example, a waste container or tip box.

In some embodiments, the handheld pipette apparatus may be adapted to be picked up by an external robot. This robotic arm would have the tooling adapter to pick up and move the handheld pipette apparatus. The robotic movements would be loaded from a recipe, or pre-saved method, that was originally programmed be the operators manual movements. In this case, the operator could manually process a procedure and then have the robotic arm reproduce this procedure.

The system described herein also supports plate replication. As used herein, the term "plate replication" refers to a process of replicating a single plate to one or more destination plates. In some embodiments, the source and destination plates may have the same format or different formats. In some implementations, a single source of tips may be used for all destination plates although each plate may support different volumes of liquid.

In addition, the system provides for liquid transfers from a single source plate to numerous destination plates and vice versa. The system also supports serial dilution in which a single source (row or column) is dispensed or aspirated to/from multiple destination positions. For example, the first aspiration may be from a single source or multiple sources. The liquid may then be dispensed to a first destination position. The first destination position may subsequently become the aspirate location for the next transfer and so on. The system also supports new tips for transfer operations and enables liquids to be mixed prior to a liquid being aspirated or after a liquid is dispensed and for such steps to be tracked for verification.

In addition, the system may run a recipe/method, from a secure network drive from a remote or common location with the workbench. The system can load, or pull up, pre-validated methods that are stored on a secured network drive. This networked loaded recipe standardizes how samples are processed across different operators, different labs and different sites. With the use of the handheld pipette apparatus, there is no operator technique involved for liquid handling variability issues and no incorrect positional transfers with the vision system validation. This gives companies and government services, like the ATF and FBI crime labs, the ability to standardize processes and document every liquid transfer with quality and defensible data.

In addition, the system provides for tube to plate or tube to tube transfers where the tubes may be manually scanned or otherwise placed at known locations in a tube rack and all transfers may be validated through the vision system and handheld pipette apparatus sensor system. For example, forensic methods needing a tube of blood may be processed by the operator manually scanning the tubes and placing them into a tube rack on the system deck workspace. The vision system will track the bar code and position that the operator places the tube in the rack. The operator then proceeds to transfer the blood from the tube to either another tube pre-scanned in a rack or a microplate that has a pre-scanned bar code and the entire process is documented and validated.

In addition, clinical human samples may be processed using a similar method to the forensic blood transfer method explained above. In this method, human samples of blood, plasma, tissue, or of a liquid biopsy may be transferred using this system to fully document and validate the process for FDA Phase 3 Clinical Trials or Invitro Clinical Diagnostics. Numerous other categories of assays, protocols or other methods can similarly be verified by the vision system of this invention.

OBJECTS OF THE INVENTION

Accordingly, a primary object of the present invention is to provide fluid sample processing environment which can verify fluid sample processing has been conducted according to parameters of a fluid sample processing protocol.

Another object of the present invention is to provide a fluid sample processing system which uses at least one camera to verify a location of a tip of a pipette during fluid sample processing, for use in verifying that processing protocols have been properly followed.

Another object of the present invention is to provide a method and apparatus for blocking improper fluid collection/aspiration functions with a manual pipette if they are outside of a fluid sample processing protocol, such as involving incorrect location for a tip of a pipette or an incorrect function of the pipette, such as aspiration when dispensing is called for, or aspiration/dispensing of incorrect volumes of fluid.

Another object of the present invention is to provide a fluid sample processing system which provides instructions to an operator of a manual pipette and verifies that instructions were properly executed.

Another object of the present invention is to provide a camera system which takes images of a fluid sample processing location at an instant when a fluid transfer function is executed by a pipette to record pipette tip location at the moment of aspiration/dispensing.

Another object of the present invention is to provide a method for validation of fluid sample processing utilizing at least one camera to record pipette tip position during at least one instant of the fluid sample processing operation, and typically during multiple stages thereof or throughout the entire operation.

Other further objects of the present invention will become apparent from a careful reading of the included drawing figures, the claims and detailed description of the invention.

DESCRIPTION OF THE PREFERRED EMBODIMENT

Figure 1:
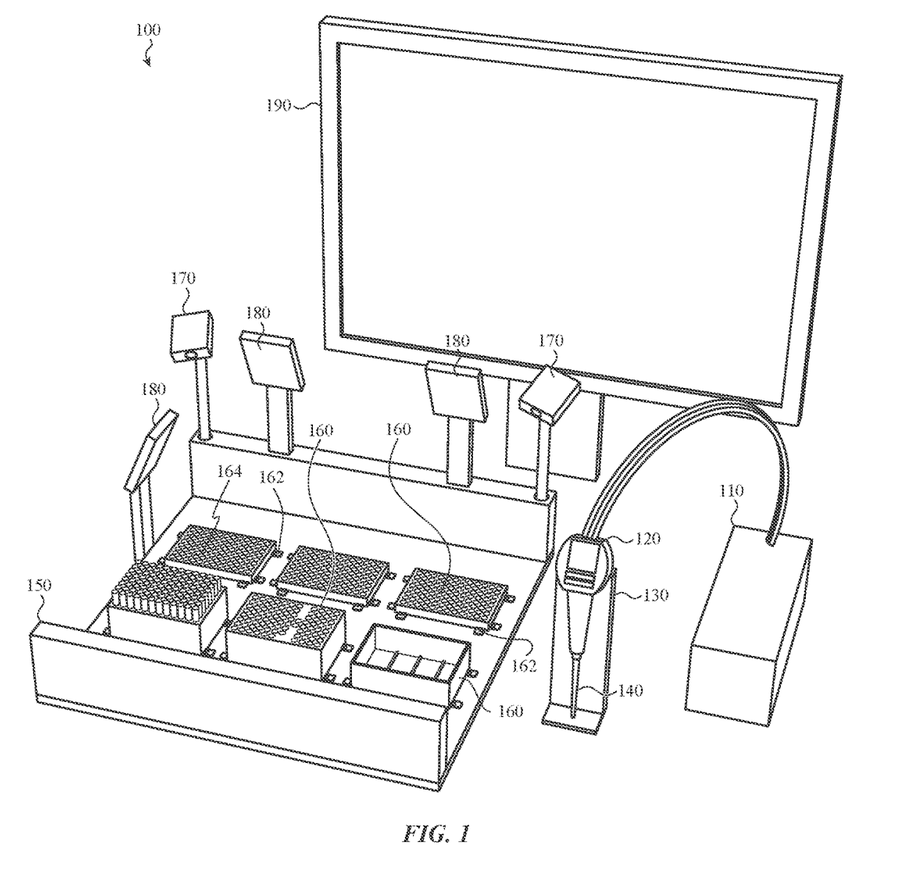
FIG. 1 is a perspective view of a system incorporating a workbench, a handheld pipette apparatus and a vision system according to this invention.

Referring to the drawings, wherein like reference numerals represent like parts throughout the various drawing figures, reference numeral 100 (FIG. 1) is directed to a system for processing a fluid sample in a verified manner. FIG. 1 illustrates an exemplary embodiment system 100 for collecting and monitoring the aspiration and dispensing of liquid using a handheld pipette apparatus 120, such as described above.

As shown in FIG. 1, the system 100 includes a pipetting controller 110 and the handheld pipette apparatus 120. The handheld pipette apparatus 120 may be connected to the pipetting controller 110 wirelessly, or using various communication, air, power and/or pressure and vacuum tubes. The pipetting controller 110 may be used to monitor and control the dispensing and aspiration of liquid such as described above, or just for passive documentation of pipette 120 tip 140 position (and optionally orientation) at meaningful times, such as when aspirating or dispensing.

The handheld pipette apparatus 120 may be stored in a stand 130. One or more sensors associated with or otherwise integrated with the stand 130 (and/or the handheld pipette apparatus 120) may sense when the handheld pipette apparatus 120 is secured or is otherwise placed on the stand 130 and when the handheld pipette apparatus 120 has been removed from the stand 130. In one embodiment, when the sensors detect that the handheld pipette apparatus 120 has been removed from the stand 130, the pipetting controller 110 may enable the handheld pipette apparatus 120 to aspirate and dispense liquid in the manner described above. In addition, the sensors may also indicate that the vision system and lighting system associated with the system 100 should also begin monitoring the movement and/or location of the handheld pipette apparatus 120, such as described above.

As shown in FIG. 1, the handheld pipette apparatus 120 includes a pipette tip attachment 140 and tip eject sleeve. In some embodiments, the pipette tip attachment 140 may be tapered such that pipette tips having various sizes may be coupled to the handheld pipette apparatus. The tapered configuration may also reduce the air volume between the distal end of a disposable pipette tip and the sensors that monitor the flow rate of the liquid. The pipette tip attachment 140 may also function to eject the tip from the tip adapter end. In addition, the stand 130 may be used to change pipette tips that are coupled to the handheld pipette apparatus 120. The system 100 can log and validate details such as when the tip adapter 140 had a new pipette tip attached to the pipette 120 and the location where the new tip was taken from.

The system 100 also includes a deck workbench 150. Preferably, the workbench 150 has a staging area for storing or otherwise placing the various test tubes, racks, plates, trays 160 and other labware which can hold volumes of fluid to be used as part of the recipe, testing protocol, assay, etc. Also, equipment such as disposable tips on a tip support stand can be located in this staging area. In some embodiments, the staging area workbench 150 may contain between 1-18 positional locators 162 that hold the labware such as, for example, disposable tip racks, liquid reservoirs, trays, tube racks and microplates. The workbench may be setup using locators 162 that may be screwed or pinned to the deck or implement magnets within both the deck and the locators to have a flat surface that is easily cleaned and sterilized. The locators 162 cause position of the "labware" to be at precise locations that can be correlated with the pipette 120 position information to determine what labware was present when the pipette 120 performed some step in the process (e.g. aspiration, dispensing, tip exchange, mixing, etc.). In some embodiments, shorter plates are placed nearer the camera 170 (or cameras) in order to enable the camera 170 to capture images of other labware further from the camera 170.

As described above, the labware may include bar codes that are readable by the cameras such as described above, such as to automate the process of correlating location information with labware details and fluid content details. The lights 180 may be used to increase visibility for the cameras 170 placed in various positions to illuminate the containers, racks, trays, plates and other labware to be used on the system. The lighting acts to differentiate the workbench 150 labware from the disposable pipette tip 140 on the handheld device 120. The light can be visible light or some other non-visible light frequency that is visible to the cameras 170.

The system 100 may also include a computing device 190. The computing device 190 may be used to output various notifications to the operator on a display thereof, including the volumes of liquid dispensed, the volumes of liquid aspirated, errors in recipes or methods and so on. The computing device 190 may also control the cameras 170, the lights 180 and provide instructions to the pipetting controller 110. The controller 110 could be merely software running on the computing device 190 or hardware coupled to the computing device 190.

In some implementations, the pipetting controller 110 includes a vacuum pump and reservoir, a pressure pump and a reservoir, a microprocessor controlling unit and a power supply. The pipetting controller 110 may be communicatively coupled to the handheld pipette apparatus 120 such as described above.

Figure 2:
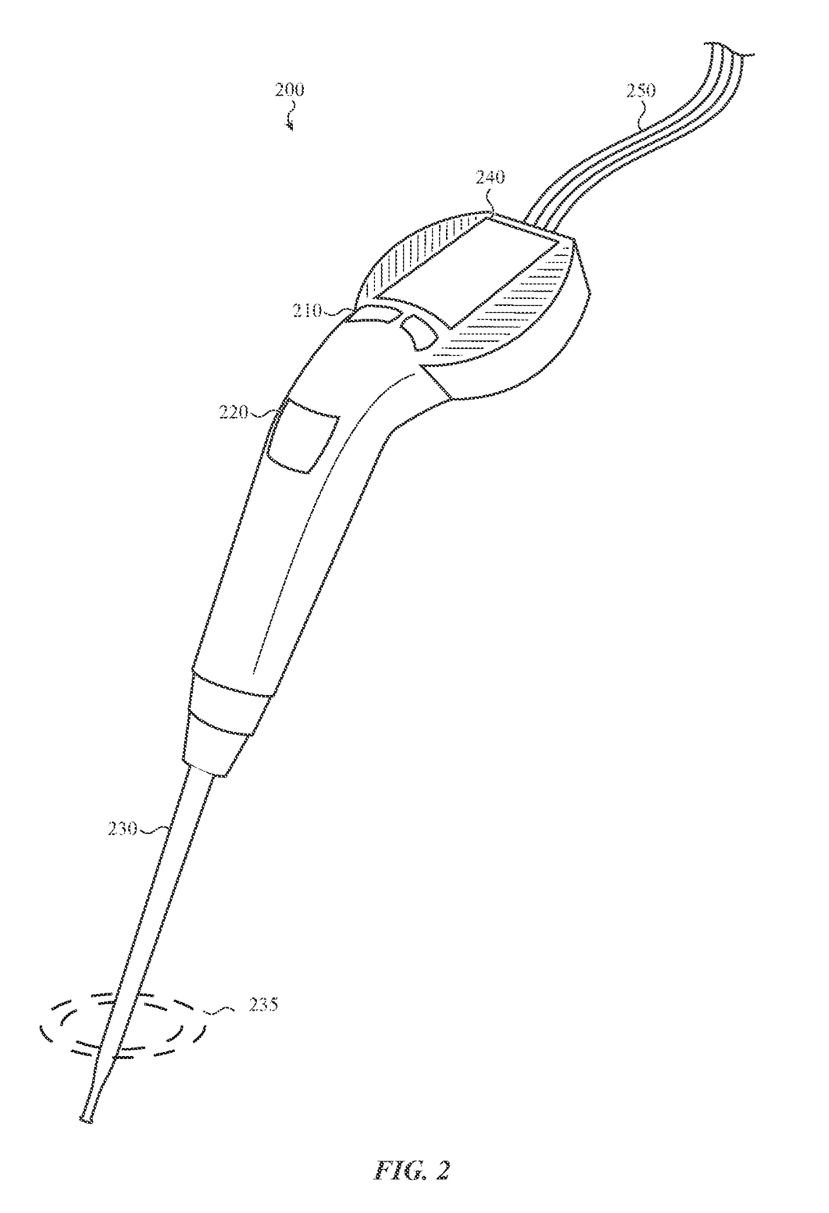
FIG. 2 is a perspective view of an example handheld pipette apparatus that may be used with the system shown with respect to FIG. 1.

FIG. 2 illustrates a handheld pipette apparatus 200 according to some embodiments of the present disclosure. The handheld pipette apparatus 200 may be similar to the handheld pipette apparatus 120 described above. The handheld pipette apparatus 200 includes various buttons 210 for aspirating, dispensing, and/or mixing a liquid. The handheld pipette apparatus 200 also includes a pipette tip adapter 230 that removably supports a tip which is typically disposable and replaceable with other tips of the same or different sizes and configurations. The tip can be ejected off of the tip adapter 230 using an eject button 220. A ring 235 can be fixed to or removably attachable to the tip adapter 230 (or disposable tip), and of a unique color or other visually distinct character, to enhance tip 230 visibility to the cameras 170.

The handheld pipette apparatus 200 may also include a display 240. The display 240 may show the mode of operation of the handheld pipette apparatus 200, whether the handheld pipette apparatus 200 is in a correct position or location on the staging area of the deck 150, or provide other such notifications. A cord 250 having various vacuum and pressure tubes, as well as various power and communication cords, may be coupled to the handheld pipette apparatus 200. As an alternative, the pipette 200 could be wireless and generate vacuum/pressure through onboard equipment and communicate wirelessly to other parts of the system 100.

As described above, the handheld pipette apparatus 200 may be used to automatically fill (aspirate) a pipette tip with a desired amount of liquid. This liquid may then be dispensed into various wells of a tray such as described. The amount of liquid aspirated and dispensed can also be validated by the system 100 such as described above.

More specifically, the handheld pipette apparatus 200 may include or otherwise be associated with a micro-controller that detects the actuation of the buttons 210. For example, when an aspirate button is actuated, the vision system is activated and liquid is drawn into the pipette tip. Likewise, when a dispense button is actuated, the vision system is activated and liquid is dispensed from the pipette tip. The micro-controller may also be configured to communicate with the system computer system 190 and the pipetting controller 110 to coordinate pipetting activities. In some embodiments, when a pipette tip is attached to the pipette tip adapter 230 of the handheld pipette apparatus 200, a pressure or hall sensor may be triggered to activate the vision system for tip validation or otherwise ensure that the tip is uncontaminated and/or properly installed.

The aspirate button causes liquid to be drawn into the pipette tip. It also signals the microprocessor to communicate with the pipetting controller 110 to monitor the volume of liquid being drawn into the tip as well as the volume that is accumulating in the tip. Actuation of the aspirate button also causes the vision system 170 and lighting system 180 to validate and/or record the well/tube (or other) location in the plate or tray at one of the multiple locations on the deck 150. The vision system will validate this process using the two stages described above.

In some embodiments, a dial may be present on the handheld pipette apparatus 200. The dial may be used to indicate the amount of liquid that will be aspirated or dispensed by the handheld pipette apparatus 200. In other embodiments, the desired volume may be input on an associated computing device 190 or controller 110 or a display of the pipette 120. Pressing the aspirate button also enables the micro-controller to reach the target volume set by the operator.

As the liquid is being aspirated or dispensed, the vision system 100 will validate source well/tube position, etc. if a stored recipe/method is being executed. The system 100 will also output an error if an incorrect source or destination position of the handheld pipette apparatus 200 is detected. The system 100 may deactivate the pipette buttons 210 on the handheld pipette apparatus 200 until a proper location is accessed. The computer apparatus 190 may also display the target and actual volume aspirated into the pipette tip on the computer screen interface and/or on the display screen 240 of the handheld pipette apparatus 200.

The handheld pipette apparatus 200 and the associated computing system may also record the fill volume as well as the source plate/rack ID bar code and the source volume well/tube number in a memory device.

When the dispense button is actuated, the micro-controller of the handheld pipette apparatus 200 communicates with the pipetting controller 110 to monitor liquid evacuation from the pipette tip and determines when the desired aliquot has been dispensed. Actuation of the dispense button also causes the vision and lighting system to validate and record the well/tube location in the plate or tray. The vision system may have two validation stages such as described above. The dispense button may also be used to signal the micro-controller to communicate with the pipetting controller 110 to record the target and actual volume of the desired aliquot in a memory.

When the tip eject button 220 is actuated, the handheld pipette apparatus 200 may activate software to record the tip ejection to ensure that contaminated tips are not reused in a subsequent liquid transfer step. This button may also signal the recording of the source plate/rack ID bar code and destination volume well/tube number in a memory device.

Figure 3:
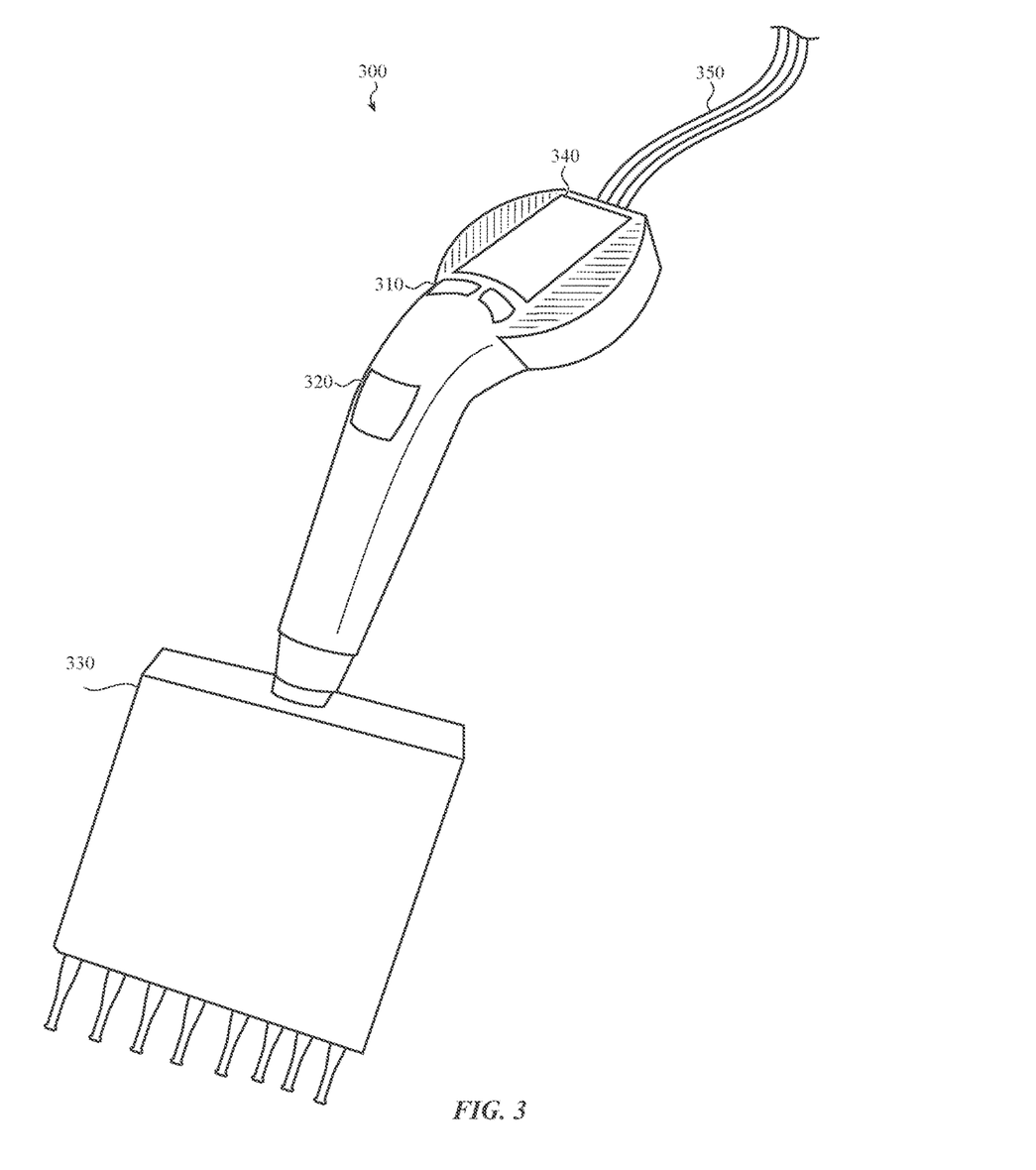
FIG. 3 is a perspective view of an example of a multi-channel handheld pipette apparatus used with the single channel for high speed liquid transfers to wells in a microplate, or test tubes in a uniform rack.

With particular reference to FIG. 3, a multi-channel pipette 300 is disclosed as an accessory to substitute for or use along side of a pipette 200 (FIG. 2) or the pipette 120 (FIG. 1). This multi-channel pipette 300 includes an eject button 320, operation buttons 310, a display 340, and a tip assembly 330, as well as associated lines 350 (in non-wireless embodiments) which are each similar to those of other embodiments described herein, except that the tip assembly 330 is configured for faster operations and higher throughput and improved duty cycle.

The multi-channel tip assembly 330 preferably includes an array of tips which are in a line and with spacing therebetween which matches spacing between wells 164 (FIG. 1) on a plate-type fluid support 160 or which align with multiple test tubes housed within a test tube rack type fluid support 160. Most preferably, such fluid supports 160 are provided in rectangular arrays with a certain number of uniformly spaced fluid locations in each row and in each column. Preferably the number of tips on the tip assembly 330 of the multi-channel pipette 300 match either a total number of fluid locations in a row or a total number of locations in a column of one such fluid support 160. In this way, the multi-channel tip assembly 330 of the multi-channel pipette 300 can aspirate or dispense fluid in multiple locations associated with the fluid supports 160 simultaneously, greatly increasing speed with which laboratory procedures performed by the system 100 can be achieved.

As an alternative, the multi-channel tip assembly 330 could have a number of tips which is some whole fraction of the number of fluid supports 160 in a row or in a column. For instance, if the fluid support 160 in the form of a microplate could have an 8×12 array of wells 164 provided as fluid locations within the tray type fluid support 160. The tip assembly 330 could then have eight tips for maximum effectiveness, but could also be efficient with four tips or two tips. Other less efficient numbers of tips could also be provided and still provide some benefit over single tipped pipettes 120, 200. As another option, the tip assembly 330 could have a two-dimensional array of tips such as a 2×8 array (or even an 8×12 array) so that fluid locations can be even more expeditiously accessed.

With the multi-channel pipette 300, the vision system 100 utilize the cameras 170 not only to pinpoint the location of the tip assembly 330, but also the orientation of the tip assembly 330, so that well or other fluid location specific information is accurately gathered by the vision system disclosed herein to facilitate and verify accuracy of tip location adjacent to fluid locations.

Figure 4:
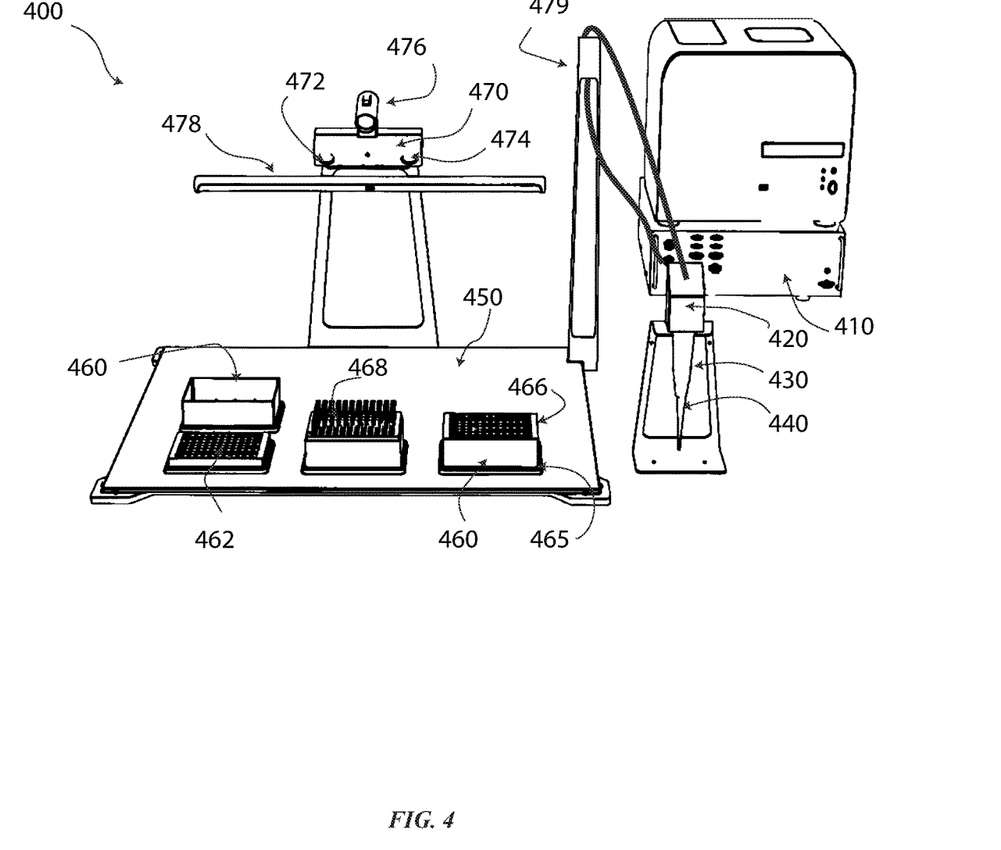
FIG. 4 is a perspective view of an alternative system to that depicted in FIG. 1, but with a stereoscopic vision subsystem.

With particular reference to FIG. 4, an alternative embodiment system 400 is disclosed as an alternative to the system 100 (FIG. 1). In this embodiment similar structures are provided with similar reference numerals. The primary unique feature of the system 400 is the provision of a stereoscopic camera assembly 470 of two or more cameras, in place of (or in addition to) one or more separate cameras 170 (FIG. 1). Thus, this system 400 utilizes a controller 410 which interfaces with a handheld pipette 420 held upon a stand 430. A tip attach/eject sleeve 440 is provided on the pipette 420. A dock/workbench 450 is provided with multiple locators 265 where fluid supports 460, such as microplates 462, racks 466 to support test tubes 468 or other fluid supports can be precisely located, preferably in arrays of similar labware. In this manner, position information on the workbench 450 can be correlated with the containment of specific fluids or other equipment (e.g. removable tips/sleeves 440), so that particular locations detected by the camera 470 can be correlated with the aspiration or dispensing of particular liquids, or the selection of a particular tip 440, or other actions.

The camera 470 is preferably a stereoscopic camera that has a left camera sensor 472 and a right camera sensor 474 (or optionally a triscopic camera box to achieve a similar result). Optionally an auxiliary camera 476 can also be provided, such as in the form of a video camera or still camera. The camera sensors 472, 474 can be still, video or combined type cameras. The left and right camera sensors 472, 474 are spaced a known distance apart and have their signals integrated in a standardized fashion so that a three-dimensional image is constructed stereoscopically.

The overall stereoscopic camera system 470 also preferably includes a light bar 478 which extends horizontally, and optionally also a vertical light bar 479 which in this embodiment also acts as a tower to which the lines extending from the pipette 420 can attach, so that these lines stay out of the way of the workbench 450, but allow the pipette 420 to reach all of the locations on the workbench 450. If needed, a tensioning system can be provided to play out and draw up excess amounts of line to further keep these lines from being a nuisance or preventing the pipette 420 from reaching all of the required locations on the workbench 450. By providing one horizontal light bar 478 and one vertical light bar 479, shadow minimization is to a greater extent achieved than with lights of a single point, line or other limited orientation. Other lighting configurations could alternatively be provided. The system 400 can also work without lighting, relying on ambient light, infrared radiation, etc.

Figure 5:
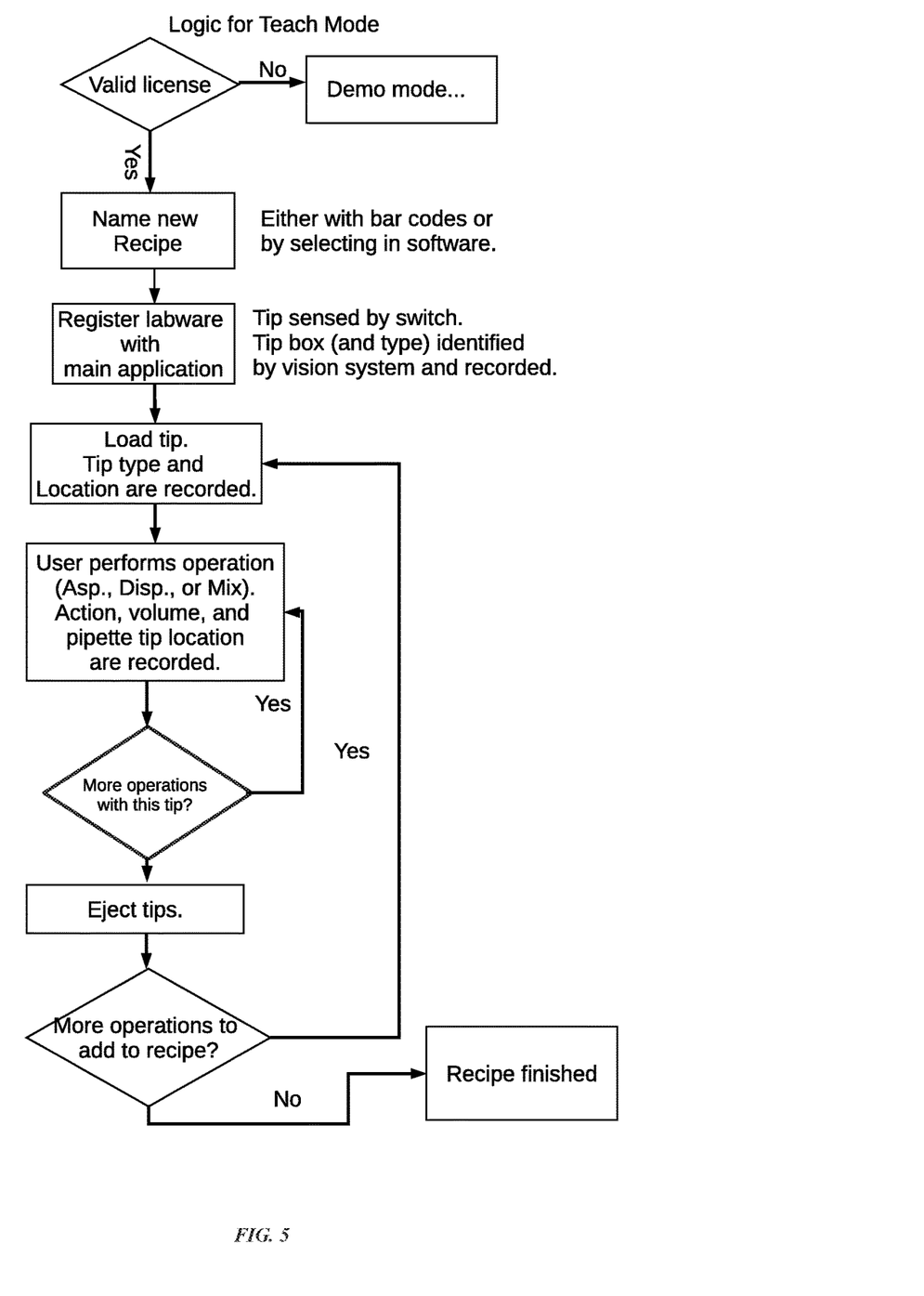
FIG. 5 is a flowchart showing operation of the system in a "teach" mode.
Figure 6:
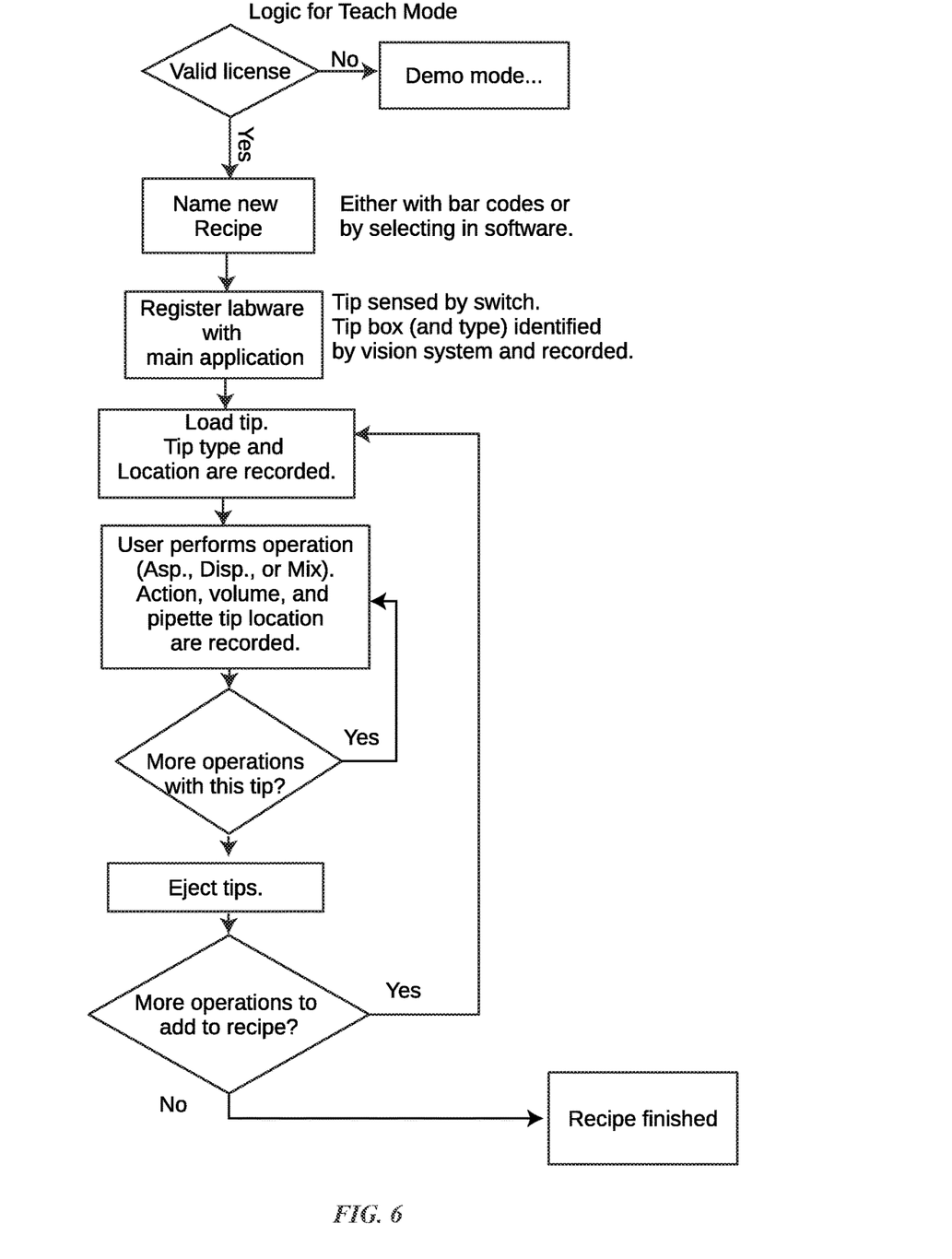
FIG. 6 is a flowchart showing operation of the system in a "recipe" mode.

With particular reference to FIGS. 5 and 6, flow charts are provided which show protocols and other methods which can be implemented by the systems 100, 400 described herein. In FIG. 5 a flow chart defines the steps in a "teach mode" according to one form of this invention. In FIG. 6 a similar flowchart, but for a "recipe mode" is depicted. As a first step disclosed in these procedures, the systems 100, 400 can be configured so that a microprocessor serial number validation system is provided. The systems 100, 400 are prevented from working unless a valid number is first inputted into the system. Such a number acts as a "key" for the system and can enable payment/billing systems, so that the systems 100, 400 generates a payment obligation for each session in which they are put to use, and also allow for case numbers or other identifying information to be logged into the various databases at the beginning of a particular session. Most preferably, the systems 100, 400 can still operate in a demo mode when no appropriate number or other key is inputted in this first step. Such a demo mode can be used for training purposes or to communicate to others how the systems 100, 400 works when in full operation.

The processes are further implemented as illustrated in the respective flow charts shown in FIGS. 5 and 6. In a teach mode (FIG. 5), one is able to teach the system 100, 400 what the proper specific locations are, volumes are, and other details are for running a particular assay, testing protocol, or other "recipe." Once the system 100, 400 has been taught the proper "recipe," this enables the system 100, 400 to then later monitor the operation of the system 100, 400 and compare it to the proper operation. If anomalies are detected, error codes can be attached to validation information, or the aspirate/dispense functions (and other functions) can optionally be prevented (at least initially), with typically the opportunity for override, but typically not allowing any tampering with the validation system which carefully logs pipette 120, 200, 300, 420 position information, volume information, and other validation information, typically also with respect to a timestamp and any fluids, etc. identified as being at any of the locations visited by the pipette 120, 200, 300, 420. Once the system 100, 400 has been "taught" a recipe/protocol, the recipe/protocol can optionally be saved and/or transferred to other similar systems 100, 400 so that the other systems 100, 400 could be preprogrammed to provide validation and other assistance with the same recipes/protocols, thus potentially having multiple recipes/protocols the systems 100, 400 are ready to support.

As shown in the flow charts, interactive information can be provided onto the display 240, 340 of the pipette 200, 300, or onto the display associated with the computing device 190 (FIG. 1). This allows a user (or other person) to be provided with instructions, and to allow for inputting of information into the system 100, 400, such as a case number, other identifying information, operator information, and any other information relevant to the recipe or other protocol being performed.

Multiple different protocols can be loaded into the system 100, 400 in preferred embodiments, so that different "recipes" can be followed by the system 100, 400, such as with the different recipes selectable from a list of recipes for which the system 100, 400 has been "taught." As an alternative, the system 100, 400 could be configured to just perform one type of recipe, such as in a particular instance where a common recipe is to be performed multiple times. In one embodiment a certified entity first "teaches" the system 100, 400 to perform the recipe and then other operators use the system 100, 400 to practice the method defined by the recipe, and with the system 100, 400 verifying proper operation.

The system 100, 400 is disclosed along with a manually held and manipulated pipette 120, 200, 300, 420. This pipette 120, 200, 300, 420 could be electric or non-electric. Also, the pipette 120, 200, 300, 420 could alternatively be robotized with appropriate carriers and actuators coupled to the pipette 120, 200, 300, 420 and causing the pipette 120, 200, 300, 420 to move to desired fluid locations and perform desired functions in an automated fashion. With such a robotic system, the cameras 170 would still be utilized to verify that the tip of the pipette 120, 200, 300, 420 truly is in the required locations but various procedures, such as an aspirate procedure, dispense procedure, mix procedure, tip change step, or other procedure was performed at a proper location. Validation that a robotic system as a variation to the system 100, 400, is properly operating could thus be provided with this invention as well.

The system described herein has various advantages over current systems. For example, the combination of the lights and cameras of the system described herein, along with a sensor controlled handheld pipette apparatus, enable the validation of information needed for quality and defensible data in a lab. This data includes information about the picture and source information of the liquid, the picture and destination information of the liquid as well as position data and actual aspiration and dispensing volumes, bar codes or plates and tips, lot numbers of tips, operator information, runtime information, method information, and time and date stamps.

In some embodiments, the handheld pipette apparatus 120 includes sensors that communication with the pipetting controller 110 that monitor the liquid as it enters and leaves the pipette tip. This monitoring may be done in real time and with a closed loop system. For example, the sensors may include a MEMS flow sensor with associated solenoid valves that provide access to vacuum or pressure that move liquid into or out of the disposable tip. Using the sensors, the system 100 described herein directly measures the flow rate of the liquid entering or leaving the pipette tip. The measured value may be accumulated over time in order to determine the actual liquid volume. As discussed above, the system 100 may incorporate temperature sensors so the system can account for changes in the viscosity of the liquids due to temperature changes.

This system is also configured to notify the operator of an error before the operator transfers liquid from one location to another location. For example, the system 100 may prevent the handheld pipette apparatus 120 from dispensing or aspirating liquid when it is determine the handheld pipette apparatus 120 is in an incorrect location compared to a recipe or other protocol. The system 100 may also flag a well or tube as being contaminated by an operator error and therefore need to be skipped or rerun.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A system for fluid sample processing validation, comprising in combination:
    a pipette including at least one tip and a fluid aspirator/dispenser coupled to said tip, said pipette having a hand grippable size and including at least one actuator thereon to cause fluid aspiration and/or dispensing relative to said tip;
    at least one target location;
    at least one camera having said at least one target location within a field of view of said camera; and
    wherein said pipette includes a plurality of buttons thereon for actuation of said fluid aspirator/dispenser, said camera image collection actuator at least indirectly coupled to at least one of said buttons for camera image acquisition when at least one of said buttons is actuated.

2. The system of claim 1 wherein a camera image collection actuator is coupled to said at least one camera to cause said at least one camera to acquire an image including said target location, said actuator also coupled to said fluid aspirator/dispenser of said pipette.

3. The system of claim 1 wherein a controller is coupled to said pipette and said at least one camera.

4. The system of claim 3 wherein said camera image collection actuator is coupled to said aspirator/dispenser of said pipette, said at least one camera configured to acquire an image when said aspirator/dispenser is operated to transfer fluid relative to said tip of said pipette.

5. The system of claim 1 wherein said fluid aspirator/dispenser includes fluid volume control.

6. The system of claim 1 wherein said at least one target location is a known position relative to said at least one camera.

7. A system for fluid sample processing validation, comprising in combination:
    a pipette including at least one tip and a fluid aspirator/dispenser coupled to said tip, said pipette having a hand grippable size and including at least one actuator thereon to cause fluid aspiration and/or dispensing relative to said tip;
    at least one target location;
    at least one camera having said at least one target location within a field of view of said camera;
    wherein a controller is coupled to said pipette and said at least one camera, said controller including a protocol including a series of desired steps and with at least one of said desired steps to be performed at said target location, said controller inhibiting operation of said fluid aspirator/dispenser if a function not specified by said protocol is initiated; and
    wherein said fluid aspirator/dispenser of said pipette includes a signal transmitter and a signal receiver coupled to said controller, said signal transmitter sending a signal when actuation of the aspirator/dispenser is attempted, and said signal receiver receiving a signal allowing or blocking said fluid aspirator/dispenser at least partially dependent upon pipette tip location information gathered by said at least one camera.

8. The system of claim 7 wherein said controller is configured to allow function of said fluid aspirator/dispenser which are consistent with said protocol and to block functions which are inconsistent with said protocol.

9. A system for fluid sample processing validation, comprising in combination:
    a pipette including at least one tip and a fluid aspirator/dispenser coupled to said tip, said pipette having a hand grippable size and including at least one actuator thereon to cause fluid aspiration and/or dispensing relative to said tip;
    at least one target location;
    at least one camera having said at least one target location within a field of view of said camera;
    wherein said at least one target location is a known position relative to said at least one camera;
    wherein a plurality of target locations are provided within said field of view of said at least one camera, each of said plurality of target locations having a known position relative to said at least one camera, the system configured for a fluid analysis protocol to occur involving multiple different target locations for fluid transfer by said tip of said pipette, and with said at least one camera acquiring images, verifying tip location and aspiration/dispensing function, as well as a time associated with each image, for fluid analysis verification;
    wherein a plurality of cameras are provided adjacent to said plurality of target locations, each of said plurality of cameras acquiring images which are utilized together at least partially to further verify pipette tip location relative to said plurality of target locations; and
    wherein said pipette includes a plurality of tips spaced apart from each other by a known fixed distance, and with said plurality of target locations including at least some target locations which are spaced apart by a distance similar to spacing between said tips, and wherein said fluid aspiration/dispensing can occur for multiple lines of said tips and said target locations substantially simultaneously.

10. The system of claim 9 wherein said aspirator/dispenser is prevented from operating unless said at least one camera detects said tip of said pipette at a proper location for aspiration/dispensing.

11. The system of claim 10 wherein said system includes an operator communication output which communicates a warning when a fluid aspiration/dispensing function is attempted that is outside of said protocol.

12. The system of claim 10 wherein said at least one camera includes at least two cameras spaced from each other to provide a stereoscopic image.

13. A system for fluid sample processing validation, comprising in combination:
    a pipette including at least one tip and a fluid aspirator/dispenser coupled to said tip, said pipette having a hand grippable size and including at least one actuator thereon to cause fluid aspiration and/or dispensing relative to said tip;
    at least one target location;
    at least one camera having said at least one target location within a field of view of said camera;
    wherein said at least one target location is a known position relative to said at least one camera;

wherein a plurality of target locations are provided within said field of view of said at least one camera, each of said plurality of target locations having a known position relative to said at least one camera, the system configured for a fluid analysis protocol to occur involving multiple different target locations for fluid transfer by said tip of said pipette, and with said at least one camera acquiring images, verifying tip location and aspiration/dispensing function, as well as a time associated with each image, for fluid analysis verification; and wherein said pipette includes a plurality of tips spaced apart from each other by a known fixed distance, and with said plurality of target locations including at least some target locations which are spaced apart by a distance similar to spacing between said tips, and wherein said fluid aspiration/dispensing can occur for multiple lines of said tips and said target locations substantially simultaneously.

14. The system of claim 13 wherein said aspirator/dispenser is prevented from operating unless said at least one camera detects said tip of said pipette at a proper location for aspiration/dispensing.

15. The system of claim 14 wherein said system includes an operator communication output which communicates a warning when a fluid aspiration/dispensing function is attempted that is outside of said protocol.

16. The system of claim 14 wherein said at least one camera includes at least two cameras spaced from each other to provide a stereoscopic image.

* * * * *